(12) United States Patent
van Wettere

(10) Patent No.: US 8,993,635 B2
(45) Date of Patent: Mar. 31, 2015

(54) METHOD OF INCREASING OR MAINTAINING THE REPRODUCTIVE PERFORMANCE OF SOWS

(75) Inventor: William van Wettere, Freeling (AU)

(73) Assignee: Pork CRC Ltd, Roseworthy (AU)

( * ) Notice: Subject to any disclaimer, the term of this patent is extended or adjusted under 35 U.S.C. 154(b) by 182 days.

(21) Appl. No.: 13/282,682

(22) Filed: Oct. 27, 2011

(65) Prior Publication Data

US 2012/0129943 A1     May 24, 2012

Related U.S. Application Data

(60) Provisional application No. 61/408,101, filed on Oct. 29, 2010.

(51) Int. Cl.
*A61K 31/137*     (2006.01)
*A61P 13/08*     (2006.01)

(52) U.S. Cl.
CPC .................................. *A61K 31/137* (2013.01)
USPC .......................................................... 514/653

(58) Field of Classification Search
CPC .................................................... A61K 31/137
See application file for complete search history.

(56) References Cited

PUBLICATIONS

Pain et al. in Manipulating Pig Production XI, Proceedings of the Eleventh Biennial Conference of the Australasian Pig Science Association (2007), Editors: J.E. Paterson and J.A. Baker, p. 140.*
Van Wettere et al. in Manipulating Pig Production XII, Proceedings of the Twelfth Biennial Conference of the Australasian Pig Science Association, Cairns, Queensland, Australia, Nov. 22-25, 2009, p. 46.*
Wilson et al. in Swine Health and Production 1(4), 10-15 (1993).*
Pain, S.J., et al., "Supplementing lactating sow diets with ractopamine: effects on sow weight loss, milk composition and piglet growth," Manipulating Pig Production XI (2007) p. 140; cited in corresponding Australian application.

* cited by examiner

*Primary Examiner* — Dennis Heyer
(74) *Attorney, Agent, or Firm* — Millen, White, Zelano & Branigan, P.C.

(57) ABSTRACT

The present invention relates to methods and feed compositions for increasing or maintaining the reproductive performance of sows. More particularly, the present invention relates to methods of increasing or maintaining the reproductive performance of sows by administering a biologically active compound during lactation, and food compositions comprising said biologically active compound for the purposes of increasing or maintaining the reproductive performance of sows. The present invention also relates to a method of increasing or maintaining ovarian function in sows.

8 Claims, No Drawings

METHOD OF INCREASING OR MAINTAINING THE REPRODUCTIVE PERFORMANCE OF SOWS

This application claims the benefit of the filing date of U.S. Provisional Application Ser. No. 61/408,101 filed 2010 Oct. 29, which is incorporated by reference herein.

FIELD OF THE INVENTION

The present invention relates to methods and feed compositions for increasing or maintaining the reproductive performance of sows. More particularly, the present invention relates to methods of increasing or maintaining the reproductive performance of sows by administering a biologically active compound during lactation, and food compositions comprising said biologically active compound for the purposes of increasing or maintaining the reproductive performance of sows. The present invention also relates to a method of increasing or maintaining ovarian function in sows.

BACKGROUND OF THE INVENTION

Sow productivity has traditionally been defined as the number of progeny pigs weaned per sow per year. However, the length of time that sows remain productive within commercial operations also plays a major factor in their profitability and economic success. Producers are financially rewarded for having sows with an improved productive lifetime because the initial cost of the replacement gilt and associated development expenses to be spread across a greater number of piglets produced during the sow's lifetime.

Current sow culling rates are excessive and often sows are removed from the breeding population before reaching their breakeven parity. This situation can affect overall profitability. Reasons for culling sows can be attributed to genetics, reproduction, nutrition, environment, and management. However, premature culling of breeding sows tends to fall into two distinct categories:
  Very early culling of gilts and parity 1 sows on the basis of reproductive failure and locomotor problems.
  Culling around parities 3-5 for poor reproductive performance.

Therefore, reproductive failure is accepted to be the largest reason for the culling of primiparous sows.

Sow productive lifetime or length of productive life is typically measured several ways, including days of age from birth to culling, life from entry into the breeding population through culling, and the number of successful parities completed. Currently, the Australian industry average is predicted to be 30-40 pigs weaned/lifetime which is well below the potential to produce at least 80-90 pigs weaned per sow per lifetime. Similar poor sow reproductive performance is also reported in most other major pig producing countries. Therefore, pig producers are constantly looking for ways to increase sow performance and productive life.

For many years it has been thought by most within the research community that the limitation to improved reproduction is simply a matter of improving the implementation of existing knowledge to producers. However, with national herd statistics showing that reproduction is not improving, pig producers are highlighting that this approach must be combined with both large scale studies that report on longevity and research into the fundamental nutritional and management requirements, in particular because of today's genetically lean genotypes.

Studies have shown that modification of the gilt's fat reserves as she enters the breeding population through protein restriction or increased feeding levels rarely demonstrates an improvement in reproductive performance over several parities. Likewise, no improvement in reproductive performance has been seen by increasing fatness in sows fed high energy diets during successive pregnancies. Increasing protein intake in gestation and lactation has also been recently studied in young sows. While litter size born subsequent to sows being fed high protein diets during the first lactation was positively correlated with lactation lysine intake, no benefit of high protein intake on weaning to conception interval was observed.

Accordingly, there exists an ongoing need to develop new and effective methods for increasing reproductive performance in sows and therefore sow lifetime productivity.

SUMMARY OF THE INVENTION

One aspect of the present invention is directed to a method of increasing or maintaining the reproductive performance of a sow comprising administering an effective amount of a β-agonist during lactation.

Another aspect of the present invention is directed to a method of increasing or maintaining the reproductive performance of a sow comprising administering an effective amount of a β-agonist during lactation, wherein the β-agonist is ractopamine.

Another aspect of the present invention is directed to a method of increasing or maintaining the reproductive performance of a sow population comprising administering an effective amount of a β-agonist during lactation to each sow within said population.

Yet another aspect of the present invention is directed to a method of increasing or maintaining the reproductive performance of a sow population comprising administering an effective amount of a β-agonist during lactation to each sow within said population, wherein the β-agonist is ractopamine.

In another aspect the present invention is directed to a method for increasing or maintaining ovarian function in a sow comprising administering an effective amount of a β-agonist during lactation.

In yet another aspect the present invention is directed to a method for increasing or maintaining ovarian function in a sow comprising administering an effective amount of a β-agonist during lactation, wherein the β-agonist is ractopamine.

Another aspect of the present invention is directed to a method of decreasing the weaning to oestrus interval of a sow comprising administering an effective amount of a β-agonist during lactation.

A still further aspect of the present invention is directed to a method of decreasing the weaning to oestrus interval of a sow comprising administering an effective amount of a β-agonist during lactation, wherein the β-agonist is ractopamine.

A further aspect of the present invention is directed to a method of decreasing the weaning to oestrus interval of a sow comprising supplementing the lactation diet with an effective amount of ractopamine from day 1 of lactation until weaning, wherein the lactation diet is supplemented with between 5 and 20 ppm of ractopamine/unit of diet.

A still further aspect of the present invention is directed to a method of decreasing the weaning to oestrus interval of a sow comprising supplementing the lactation diet with an effective amount of ractopamine from day 1 of lactation until weaning, wherein the lactation diet is supplemented with 10 ppm of ractopamine/unit of diet from days 1 to 13 of lactation and 20 ppm of ractopamine/unit of diet from day 14 of lactation until weaning.

In a further aspect the present invention is directed to a method of increasing or maintaining the number of sows in a population which return to oestrus at weaning comprising administering an effective amount of a β-agonist during lactation, to each sow within said population.

In yet another aspect the present invention is directed to a method of increasing or maintaining the number of sows in a population which return to oestrus at weaning comprising administering an effective amount of a β-agonist during lactation, to each sow within said population, wherein the β-agonist is ractopamine.

In a further aspect the present invention is directed to a method of increasing or maintaining the number of sows in a population which return to oestrus at weaning comprising supplementing the lactation diet with an effective amount of a β-agonist from day 1 of lactation until weaning.

In a still further aspect the present invention is directed to a method of increasing or maintaining the number of sows in a population which return to oestrus at weaning comprising supplementing the lactation diet with an effective amount of a β-agonist from day 1 of lactation until weaning, wherein the β-agonist is ractopamine.

A still further aspect of the present invention is directed to a method of increasing or maintaining the number of sows in a population which return to oestrus at weaning comprising supplementing the lactation diet of each sow within said population with an effective amount of ractopamine from day 1 of lactation until weaning, wherein the lactation diet is supplemented with between 5 and 20 ppm of ractopamine/unit of diet.

A still further aspect of the present invention is directed to a method of increasing or maintaining the number of sows in a population which return to oestrus at weaning comprising supplementing the lactation diet of each sow within said population with an effective amount of ractopamine from day 1 of lactation until weaning, wherein the lactation diet is supplemented with 10 ppm of ractopamine/unit of diet from days 1 to 13 of lactation and 20 ppm of ractopamine/unit of diet from day 14 of lactation until weaning.

A further aspect of the present invention is directed to a method of increasing or maintaining the number of progeny pigs weaned per sow in subsequent pregnancies comprising administering an effective amount of a β-agonist during lactation.

A still further aspect of the present invention is directed to a method of increasing or maintaining the number of progeny pigs weaned per sow in subsequent pregnancies comprising administering an effective amount of a β-agonist during lactation, wherein the β-agonist is ractopamine.

A further aspect of the present invention is directed to a method of increasing or maintaining the number of progeny pigs weaned per sow population in subsequent pregnancies comprising administering an effective amount of a β-agonist during lactation, to each sow within said population.

A still further aspect of the present invention is directed to a method of increasing or maintaining the number of progeny pigs weaned per sow population in subsequent pregnancies comprising administering an effective amount of a β-agonist during lactation, to each sow within said population, wherein the β-agonist is ractopamine.

A further aspect of the present invention provides a method for synchronizing mating and/or artificial insemination of a sow population comprising administering an effective amount of a β-agonist during lactation, to each sow within said population.

A still further aspect of the present invention provides a method for synchronizing mating and/or artificial insemination of a sow population comprising administering an effective amount of a β-agonist during lactation, to each sow within said population, wherein said β-agonist is ractopamine.

In a further aspect the present invention provides a method for increasing the number of sows within a sow population which undergo mating and/or artificial insemination comprising administering an effective amount of a β-agonist during lactation, to each sow within said population.

In another aspect the present invention provides a method for increasing the number of sows within a sow population which undergo mating and/or artificial insemination comprising administering an effective amount of a β-agonist during lactation, to each sow within said population, wherein said β-agonist is ractopamine.

In yet, a further aspect the present invention provides a method for increasing the number of times a sow and/or sow population undergoes mating and/or artificial insemination per year comprising administering an effective amount of a β-agonist during lactation, to each sow within said population. Preferably, said β-agonist is ractopamine.

In another aspect the present invention provides a method for increasing the number of times a sow and/or sow population undergoes mating and/or artificial insemination per year comprising administering an effective amount of a β-agonist during lactation, to each sow within a population, wherein said β-agonist is ractopamine.

In a further aspect the present invention is directed to a feed composition comprising an effective amount of a β-agonist wherein said effective amount increases or maintains the reproductive performance of a sow.

In a still further aspect the present invention is directed to a feed composition comprising an effective amount of a β-agonist wherein said effective amount increases or maintains the reproductive performance of a sow and wherein said β-agonist is ractopamine.

DETAILED DESCRIPTION OF THE INVENTION

As stated hereinbefore, reproductive failure is one of the largest reasons for culling of primiparous sows. The present invention is predicated on the discovery that administration of the β-agonist ractopamine to sows during lactation reduces maternal weight loss and improves subsequent reproductive performance.

Accordingly, one aspect of the present invention is directed to a method of increasing or maintaining the reproductive performance of a sow comprising administering an effective amount of a β-agonist during lactation. Preferably, said β-agonist is ractopamine.

Reference to a "sow" should be understood as a reference to a female pig which has been mated one or more times. Reference to a "gilt" is reference to a female pig which has not yet been mated or has just been mated but which has not yet produced progeny pigs. Reference to a "pig" should be understood as a reference to all pigs, for example, gilts, sows, hogs, boars and barrows. The skilled person will be well aware that in the context of the present invention the term "pig" is synonymous with swine. A "progeny pig" or "piglet" refers to the offspring produced by a sow.

As stated hereinbefore, sow productivity is traditionally defined as the number of progeny pigs weaned per sow per year. However, the length of time that sows remain productive within commercial operations also plays a major factor in their profitability and economic success. This factor depends on the number of successful parities completed. Accordingly, reference to reproductive performance in the context of the present invention should be understood as reference to both the number of progeny pigs weaned per sow per year, and reference to the number of progeny pigs weaned per lifetime of a sow in the breeding herd (PW/LF). A number of factors can play a part in the reproductive performance of an individual sow, for example, but not limited to, the age and weight of the individual sow. Accordingly, reference to reproductive performance in the context of the present invention should also be understood as reference to the number of progeny pigs weaned, per sow population, per year.

Without limiting the present invention to any one theory or mode of action, it is thought to be the excessive mobilisation of body stores and in particular body protein during lactation that ultimately results in poor body condition at weaning and increases the likelihood of culling due to subsequent reproductive failure. Accordingly, reference to an increase in reproductive performance should be understood as reference to both an increase in the number of progeny pigs weaned per sow and/or sow population per year as well as reference to an increase in the number of progeny pigs weaned in subsequent pregnancies per sow and/or sow population as compared to a control sow and/or control population in which the β-agonist was not administered. Reference to maintaining reproductive performance in the context of the present invention should be understood to refer to the maintenance of the initial reproductive performance of a sow and/or sow population in subsequent pregnancies. Reference to the "initial reproductive performance" of a sow should be understood as reference to the sow's reproductive performance as a gilt.

Reference to a "control sow" should be understood as reference to a sow which has not received treatment in accordance with the method of the invention. Reference to subsequent pregnancies should be understood as reference to the next litter of progeny pigs produced by the sow.

It has been demonstrated that mobilisation of more than 9-12% of a sow's protein mass present at parturition results in a reduction in the number and size of ovarian follicles at weaning, follicular fluid volume and oestradiol levels, and the ability of follicular fluid to advance in vitro maturation of oocytes. In other words, a compromise of endocrine support for follicular growth and oocyte maturation. Also without limiting the present invention to any one theory or mode of action, fewer, less developed follicles being present at weaning, i.e., inadequate ovarian function may explain why the weaning-to oestrus interval may be extended and sometimes result in anoestrus. This has been found to particularly be the case in parity 1 sows.

Accordingly, in yet another aspect the present invention is directed to a method for increasing or maintaining ovarian function in a sow comprising administering an effective amount of a β-agonist during lactation. Preferably the β-agonist is ractopamine.

Reference to increasing ovarian function should be understood as reference to an increase in ovarian function as compared to a control sow in which the β-agonist was not administered. Reference to maintaining ovarian function should be understood to refer to the maintenance of the initial ovarian function of a sow in subsequent pregnancies As hereinbefore described, it is the failure of sows to return to postpartum oestrus which ultimately affects their reproductive performance. Without limiting the invention to any one theory or mode of action, the inventors have unexpectedly discovered that ractopamine, when fed to sows during lactation, is effective in improving the total number of sows within a population which exhibit oestrus at weaning.

Accordingly, reference to increasing reproductive performance in the context of the present invention should therefore also be understood as reference to an increase in the number of animals within a population which exhibit oestrus at weaning as compared to a control population to which ractopamine was not administered. Accordingly, reference to maintaining reproductive performance in the context of the present invention should also be understood to refer to the maintenance of the number of sows which exhibit oestrus at weaning in subsequent pregnancies.

Accordingly, in a further aspect the present invention is directed to a method of increasing or maintaining the number of sows in a population which return to oestrus at weaning comprising administering an effective amount of a β-agonist during lactation, to each sow within said population.

In a further aspect the present invention is directed to a method of increasing or maintaining the number of sows in a population which return to oestrus at weaning comprising supplementing the lactation diet with an effective amount of a β-agonist from day 1 of lactation until weaning.

Preferably, said β-agonist is ractopamine.

The term oestrus is well known in the art to refer to the periodic state of sexual excitement in the female of most mammals, excluding humans, that immediately precedes ovulation and during which the female is most receptive to mating. The skilled person would be well aware of the signs of oestrus and of how to determine when oestrus occurs. As used herein, the term "oestrus" refers to a sow that is receptive to mating.

While it is possible that milk can be expressed prior to parturition, without limiting the invention to any one theory or mode of action, it is the act of suckling by the progeny pigs which is the cause of depletion of body reserves and reproductive failure in subsequent pregnancies. Accordingly, reference to lactation in the context of the present invention should be understood to encompass the period following birth up until weaning of progeny pigs, during which milk is secreted. As used herein, it should be understood that the phrase "lactating sow" refers to a sow that has given birth to a litter of pigs and is presently producing milk. As used herein, the term "weaning" refers to the removal of progeny pigs from a lactating sow.

Studies have shown that it takes at least three litters before a sow provides a positive cash flow for the producer. Accordingly, without limiting the invention in any way, preferably, the increase or maintenance is of a parity 1, 2 or 3 sow. Even more preferably, the increase or maintenance is of a parity 1 sow.

As used herein, the phrase "parity 1 sow" refers to a sow that has had its first litter of pigs. The phrase "parity 2 sow" refers to a sow that has its second litter of pigs and the phrase "parity 3 sow" refers to a sow that has had its third litter of pigs, and the phrase "parity 3 or greater sow" refers to a sow that has had more than three litters of pigs.

Without limiting the present invention to any one theory or mode of action, the present inventors have determined that administration of the β-agonist ractopamine during lactation decreases the weaning to oestrus interval (WOI) of a sow and/or sow population compared to a control animal and/or control population which has not been administered the β-agonist.

Accordingly, yet another aspect of the present invention is directed to a method of decreasing the weaning to oestrus interval of a sow comprising administering an effective amount of a β-agonist during lactation.

In yet another aspect the present invention is directed to a method of decreasing the weaning to oestrus interval of a sow population comprising administering an effective amount of a β-agonist during lactation to each sow within said population.

Preferably, said β-agonist is ractopamine.

Preferably following administration of the β-agonist the WOI is <15 days. Even more preferably, following administration of the β-agonist the WOI is <10 days.

Within a commercial operation, synchronization of oestrus within a breeding herd is important from both an economic and herd management perspective. It is difficult to detect accurately the time at which either natural or artificial insemination (AI) of a sow population should occur if weaned sows are exhibiting oestrus at different times and/or individual sows within a population do not exhibit oestrus. This can result in low efficiency, particularly in preparing liquid boar semen for AI. Without limiting the present invention to any one theory or mode of action, decreasing the weaning to oestrus interval and/or increasing the number of sows within a population which exhibit oestrus allows for more efficient management of pig production. Furthermore, and also without limiting the present invention in any way, decreasing the weaning to oestrus interval means that insemination, either natural or artificial, can take place at an earlier time period and result in an increased number of progeny pigs weaned per sow/year and/or sow population/year.

The skilled person would clearly understand that reference to natural insemination is reference to a natural mating of the sow with a boar, while reference to artificial insemination is reference to insemination of the sow with boar semen by artificial means, which means could be any means known within in art.

Accordingly in a further aspect the invention provides a method of improving the reproductive performance of a sow population comprising the steps of:
(i) administering an effective amount of a β-agonist to a sow population during lactation such that the sow population exhibits a decreased weaning to oestrus interval compared to a sow population which has not been administered the β-agonist; and
(ii) inseminating sows in said sow population which exhibit oestrus.

Also without limiting the present invention to any one theory or mode of action, the present inventors have determined that administration of the β-agonist ractopamine during lactation increases or maintains the number of progeny pigs weaned per sow and/or sow population in subsequent pregnancies.

Accordingly, in another aspect the present invention is directed to a method of increasing or maintaining the number of progeny pigs weaned per sow in subsequent pregnancies comprising administering an effective amount of a β-agonist during lactation.

In another aspect the present invention is directed to a method of increasing or maintaining the number of progeny pigs weaned per sow population in subsequent pregnancies comprising administering an effective amount of a β-agonist during lactation, to each sow within said population.

Preferably, said β-agonist is ractopamine.

As detailed hereinbefore, the applicants have determined that administration of the β-agonist ractopamine to lactating sows increases or maintains reproductive performance. The pharmacological activity of β-agonists like ractopamine is to activate adrenergic beta-receptors. Without limiting the present invention to any one theory or mode of action, activation of adrenergic beta-receptors leads to increased intracellular concentration of cyclic adenosine monophosphate (cAMP), which triggers various events in various cells and organs. Cellular responses to beta-receptor activation include for example lipolytic activity in adipose tissues, smooth muscle relaxant activity in the bronchi and increased frequency of contractions in the heart. Accordingly, in the context of the present invention, while ractopamine is the preferred β-agonist and preferably in the form of ractopamine hydrochloride. It will also be understood by the skilled person that any β-agonist which exhibits the same properties as ractopamine could be used. For example and without limiting the present invention in any way, other β-agonists which may be used include salmeterol, formoterol, bambuterol, clenbuterol and/or derivatives thereof.

The chemical structures of some β-agonists comprise at least one asymmetric carbon atom, and such drugs commonly exist in optically active isomeric form, with the chiral carbon atom having (R) or (S) configuration. Compounds with two chiral centres, such as ractopamine, have four isomers, which are the RR-, SS-, RS-, and SR-isomers. Accordingly, it should be understood that reference to a β-agonist, for example ractopamine, in the context of the present invention is reference to a mixture of 1 or more of the isomers of said β-agonist. Preferably, the β-agonist is ractopamine and is a mixture of all four isomers of ractopamine in approximately similar concentrations (i.e., the racemate).

The terms "β-agonist", "ractopamine" or "isomer" as used herein refer not only to the free base, but also to acid addition salts or solvates thereof. Acid addition salts include, for example addition salts prepared with various acids, for example, hydrochloric acid, hydrobromic acid, sulphuric acid, phosphoric acid, nitric acid, or organic acids, such as citric acid, fumaric acid, tartaric acid, acetic acid, maleic acid, benzoic acid, p-toluenesulphonic acid, methanesulphonic acid, and the like. In relation to orally administrable forms, such as in a feed composition or premix, preferably the ractopamine is the hydrochloride salt form. Hydrate forms and polymorphs are also included in the present invention; particularly forms that can be manufactured as dry powder or forms that are water-soluble. Reference is made to Merck Index 11th edition (1989) items 9089, 209, 3927, 4628, 8223, 5053, 5836, 8142, 2347, 7765, 1840, 9720, 7461, 1317, 4159, and 963 and references cited therein and, to Am. Rev. Resp. Dis. 1988, 137: (4; 2/2) 32.

As used herein, the term "effective amount" or the like refers to an amount of a β-agonist, such as, for example ractopamine, that is sufficient to obtain a sufficient, sought-after, expected or wanted beneficial effect. In the context of the present invention and with regard to sows, a sufficient beneficial effect is considered to be present, if an increase or maintenance of reproductive performance as herein before defined is achieved. Preferably, said reproductive performance is an increase or maintenance of ovarian function. More preferably, said reproductive performance is an increase or maintenance of the number of sows which return to oestrus within a sow population. Preferably, said reproductive performance is a decrease in the weaning to oestrus interval of a sow and/or sow population. In another preferred embodiment, said reproductive performance is an increase or maintenance of the number of pigs weaned/sow and/or sow population.

As will be realised by those skilled in the art, the amount of β-agonist administered will depend on the duration of the treatment and numerous other factors as, for example, but not limited to, the weight of the individual sow, age of the sow and the chosen administration regime, as well as the form in which it is administered, this amount being easily determined by the person skilled in the art by routine methods. It is expected that the amount will fall into a relatively broad range that can be determined by routine trials.

In general, the doses of the ractopamine to be administered to sows may as an example be 5 to 200 mg/animal/day. It is common and it may be found advantageous to change the feed inclusion of ractopamine during the treatment period and all changes in the doses administered to the animals will of course influence the total consumption per animal of active ingredient. In the present method, ractopamine can be administered by any suitable means, including parenterally, transdermally, subcutaneously, intravenously, intramuscularly, orally, topically, nasally, rectally, by inhalation or via implanted reservoirs or pellets containing the drug. A preferred route of administration is the oral route, with the drug mixed into the feed or the drinking water of animals.

Accordingly, another aspect of the present invention relates to feed compositions including an admixture of feed materials containing ractopamine. Such an admixture is preferably in the form of a premix comprising ractopamine and other components, the determination of which would be well within the capabilities of the person skilled in the art. Said premix is preferentially administered in the feed to animals that are being given a diet, consisting of protein-containing food materials.

Accordingly, in another embodiment, the invention provides a premix including ractopamine, said premix being capable of increasing or maintaining reproductive performance. The amount of ractopamine will be generally chosen to provide from a total of about 5 to about 200 mg of ractopamine/animal/day. Preferably, the amount of ractopamine administered is between 5 to about 10 mg of ractopamine/animal/day.

A commercially available formulation of ractopamine is PAYLEAN® (Elanco) which comes as a solid dry premix comprising 20 g/kg of ractopamine hydrochloride with ground corncobs. Without limiting the present invention in any way, for feeding to sows, the dry premix is typically thoroughly mixed by the consumer into appropriate solid feed ingredients to obtain ractopamine hydrochloride amounts of 9-18 grams/ton. Accordingly, in a preferred embodiment of the invention, the premix of ractopamine is PAYLEAN®.

Diluents suitable for use to make up the feed compositions may include the following: alfalfa meal, soybean meal, cottonseed oil meal, linseed oil meal, sodium chloride, cornmeal, cane molasses, urea, bone meal, corncob meal, rice kernel and the like.

Since ractopamine is chemically stable in water, in an alternative embodiment the ractopamine may be administered in the drinking water. In this case, said premix of ractopamine can be prepared, containing a fixed concentration of ractopamine in a dry, water-soluble carrier or in a suitable volume of a fluid, such as water, which, in turn, can be added to the drinking water of the animals, by adding said premix volume directly to the drinking water of the animal or by adding said premix to an automatic drinking system for animals.

Formulations for oral use of ractopamine may also be presented as chewing tablets, or as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil. Tablets may be uncoated or they may be coated using known techniques, optionally to mask taste, delay disintegration and delay absorption in the gastrointestinal tract and thereby provide a sustained action over a longer period of time, such as for examples one or more days. For example, a time delay material such as glyceryl monostearate or glyceryl distearate may be employed.

As hereinbefore described, the β-agonist, preferably ractopamine, may be in the form of a premix. Such premix may take the form of powders, dispersible powders or granules suitable for preparation of an aqueous suspension by addition of water, or for the addition to a feed composition. Formulation as a suspension provides the active ingredient in admixture with a dispersing or wetting agent, suspending agent and one or more preservatives. Suitable dispersing or wetting agents are, for example, naturally-occurring phosphatides, as e.g., lecithin, or condensation products of ethylene oxide with e.g., a fatty acid, a long chain aliphatic alcohol or a partial ester derived from fatty acids and a hexitol or a hexitol anhydride, for example, polyoxyethylene stearate, polyoxyethylene sorbitol monooleate, polyoxyethylene sorbitan monooleate, etc. Suitable suspending agents are, for example, sodium carboxymethylcellulose, methylcellulose, sodium alginate, etc.

Additionally, other preferred forms of administration are by inhalation or by transdermal delivery systems or subcutaneous delivery systems, which will reduce or avoid gastrointestinal metabolism and hepatic first-pass metabolism by metabolising enzymes; such delivery systems may be designed to prolong the absorption or decrease the peak plasma drug concentration or to increase the exposure of the animal to the drug (increased AUC, meaning Area Under a Curve, where plasma drug concentration has been plotted over time).

Preparations of ractopamine may also be administered parenterally (intravenous, intramuscular, subcutaneous or the like) in dosage forms or formulations containing conventional, non-toxic pharmaceutically acceptable carriers and adjuvants. The formulation and preparation of such compositions is well known to those skilled in the art of pharmaceutical formulations. For parenteral administration ractopamine preparations may also be prepared in the form of a paste or pellet and administered as an implant.

As an alternative to a paste, pellet or subcutaneous implant, parenteral administration may involve injection of a solution, containing sufficient amount of ractopamine to provide the animal with 5 to 200 mg/day of the active ingredient.

In the methods of the present invention, the skilled person would be well aware that the β-agonist can be administered together with one or more other active compound(s). Compounds that improve or prolong the therapeutic effect of β-agonists, e.g. compounds that delay or inhibit the absorption or the metabolic degradation of the compound, may also be co-administered with the β-agonist to further improve the therapeutic activity. Other drugs such as for example other growth promoting agents and antibacterial compounds or immuno-stimulating compounds may be combined with the selected drug of the present invention to obtain improved health of the animal or improved activity of the formulation. It should be understood that supplementary ingredients could also be incorporated into the β-agonist preparations, the determination of which would be well within the capabilities of the person skilled in the art.

The base diet of the present invention can be any typical pig diet known in the art, but will preferably be those specially formulated for lactating sows.

In formulating the diets for lactating sows, a person of skill in the art can use the general knowledge in the art. For example, the Nutrient Requirements of Swine Nutrient Requirements of Domestic Animals, Number 3, 9$^{th}$ rev. ed. (National Academy of Science, Washington, D.C.: 1988), can be consulted to determine the amino acids, mineral elements, vitamins, and other dietary requirements for sows as a function of weight. The diet can contain between 5 and 30% by weight crude protein and be formulated for the specific use as a lactation diet. For example, an exemplary lactating sow diet may contain from about 600 to about 1800 g/hd/day of crude protein, from about 30 to about 70 g/hd/day of lysine, from about 35 to about 55 g/hd/day of calcium, and from about 30 to about 50 g/hd/day of phosphorus.

A further example of recommended daily nutrient levels during lactation expressed in grams per head per day, except where noted otherwise, is shown in Table 1.

TABLE 1

| COMPONENT | LACTATION |
|---|---|
| Crude Protein | 899 |
| Lysine | 44 |
| Tryptophan | 11 |
| Threonine | 32 |
| Minerals | |
| Calcium | 48 |
| Phosphorus | 43 |
| Salt | 27 |
| Copper, mg | 90 |
| Iodine, mg | 1.6 |
| Iron, mg | 900 |
| Manganese, mg | 216 |
| Selenium, mg | .54[b] |
| Zinc, mg | 900 |
| Vitamins | |
| Vitamin A, IU | 60,000 |
| Vitamin D, IU | 9,000 |
| Vitamin E, IU | 240 |
| Vitamin K,[c] mg | 24 |
| Riboflavin, mg | 45 |
| Niacin, mg | 270 |
| d-Pantothenic Acid, mg | 156 |
| Vitamin B$_{12}$, mg | .18 |
| Folic Acid, mg | 9 |
| Biotin, mg | 1.2 |
| Choline, mg | 3,000 |

[a] Legal addition if fed 1.8 kg/hd/day.
[b] Assumes at least 5.4 kg/day feed intake of a diet containing .80% lysine.
[c] Menadione sodium bisulfite (MSB) or equivalent.

The skilled person would be well aware that other feed components may be added to the lactation diet, for example, but not limited to, milo or corn, soybean meal, monocalcium phosphate, Limestone, salt, vitamins, Trace minerals, selenium. The feed schedule and feed rates used with the present method can be any standard schedule and rate used in the art. Generally, lactating sows are generally fed from about 3 to about 7 kg of the diet per day, and preferably from about 5.5 to about 6.5 kg per day. Generally, the feed is administered from 1 to 2 and up to 4 times a day. Accordingly, reference to a unit of diet in the context of the present invention should be understood as reference to the amount of β-agonist included in the average daily feed intake of a sow.

Without limiting the present invention to any one theory or mode of action the present inventors have determined that administration to a sow of 10 ppm of ractopamine/unit of diet from day 1-13 of lactation followed by administration of 20 ppm of ractopamine/unit of diet from day 14 of lactation until weaning, increases or maintains reproductive performance as herein before defined.

Accordingly, yet another aspect of the present invention is directed to a method for increasing or maintaining the reproductive performance of a sow and/or sow population, the method comprising the steps of:

(i) administering to a sow 10 ppm of ractopamine/unit of diet from day 1 to day 13 of lactation; and (ii) administering to a sow 20 ppm of ractopamine/unit of diet from day 14 of lactation until weaning.

In a preferred embodiment, said reproductive performance is an increase or maintenance of ovarian function. More preferably, said reproductive performance is an increase or maintenance of the number of sows which return to oestrus within a sow population. Preferably, said reproductive performance is a decrease in the weaning to oestrus interval of a sow and/or sow population. Preferably, said reproductive performance is an increase or maintenance of the number of progeny pigs weaned per sow and/or sow population.

The term "ppm" refers to parts per million, more specifically to "grams per kilogram" and 10 ppm equals 0.01 gram of ractopamine per kilogram of food material.

The invention will now be described with reference to the following examples which are intended only for the purpose of illustrating certain embodiments of the invention and are not to be taken as limiting the generality of the invention previously described.

EXAMPLES

Example 1

Supplementary Ractopamine During Lactation Reduces Sow Weight Loss and Improves Reproductive Performance Sixty large white first parity sows were allocated to one of two treatment groups (n=30 sows/treatment). One group (CONT) received a standard lactation diet (0.71 g available lysine/MJ digestible energy (DE)) throughout lactation, whilst the other group (RAC) received the standard lactation diet supplemented with ractopamine at 10 ppm from d 1-13 of lactation and 20 ppm from d 14 of lactation until mating. The amount of feed offered each day was stepped up gradually, reaching 5 kg/day by d 4 of lactation, and maintained at this level for the rest of lactation. Sows were weighed and P2 backfat measured on d 1, 14 and 20 of lactation, the litter size standardised to 9 piglets within 24 hours of lactation. Sows were weaned on d 21 of lactation, with boar exposure commencing 4 d after weaning and sows artificially inseminated twice at their first oestrus post-weaning. Subsequent reproductive performance of all sows was recorded: weaning-to-oestrus interval (WOI) and second litter size. Sows failing to epress eostrus within 10 d of weaning were deemed to be anoestrus and allocated a nominal weaning-to-oestrus interval of 15 d. A general analysis of variance model was used to study the effects of RAC supplementation on sow weight loss during lactation and subsequent reproductive performance.

On d 1 of lactation, sow liveweight and P2 backfat were 177.7±2.8 kg and 21.2±1.2 mm, respectively. RAC supplementation significantly decreased (P<0.05) liveweight loss between d 15 and 20 of lactation, tended (P<0.1) to reduce P2 backfat loss over the whole lactation, and increased piglets born alive at the second litter (Table 2). A numerical decrease in WOI (6.4±0.63 vs. 7.5±0.80) and the proportion of sows exhibiting oestrus within 10 d of weaning (0.95±0.08 vs 0.75±0.08) was observed for RAC compared to CONT sows.

TABLE 2

Effect of dietary ractopamine during lactation on sow feed intake, liveweight and
P2 backfat loss, and the number of piglets born at the subsequent (second) litter

| Diet | Daily feed intake (kg/day) | Lactation weight loss (kg) | | P2 backfat loss (mm) | Piglets born at second litter | |
|---|---|---|---|---|---|---|
| | | Days 1-14 | Days 15-20 | | Total born | Born alive |
| CONT | 5.0 ± 0.14 | 7.2 ± 1.33 | 4.3 ± 0./90[b] | 3.7 ± 0.55 | 8.5 ± 0.80 | 8.1 ± 0.74 |
| RAC  | 4.9 ± 0.14 | 4.6 ± 1.41 | 1.3 ± 0.96[a]  | 2.3 ± 0.57 | 9.7 ± 0.54 | 9.5 ± 0.52 |

[a,b]Means in a column with different superscripts differ significantly (P < 0.05);
CONT, control;
RAC, ractopamine.

Example 2

Effect of Paylean Treatment During First Lactation on Maternal Muscle Catabolism and Post-Weaning Fertility This experiment was conducted at the University of Adelaide's Pig and Poultry Production Institute (PPPI) at Roseworthy, South Australia, with approval from the animal ethics committees of Primary Industries and Resources South Australia and The University of Adelaide. The experiment used sixty Large White/Landrace parity 1 sows, and was conducted in four replicates: replicates one and two were run in October and November 2006, respectively (spring); and replicates three and four were run in March and April 2007, respectively (autumn).

At entry into the farrowing shed, Sixty Large White/Landrace first parity sows were weighed, and P2 backfat and maximum eye muscle depth (MMD) measured. Sows were then stratified according to both liveweight and body composition and allocated to one of two treatment groups (n=30 sows). One group (Control) received a standard lactation diet (0.71 g avail. lys/MJ DE) throughout lactation, whilst the other group (Ractopamine) received the same standard lactation diet but supplemented with ractopamine at 10 parts per million (ppm) from days 1-13 of lactation and 20 ppm from day 14 of lactation until mating. Dietary treatments commenced on day 1 of lactation (Day 0=first 24 hours after farrowing). During lactation, the amount of feed offered each day was stepped up gradually, reaching 6 kg/day by day 7 of lactation, and was fed over three meals per day, with daily feed disappearance recorded for each sow. Weaning took place 21 days after farrowing, and between weaning and first AI sows received 3 kg/day of their respective diets. Sows were weighed, and P2 backfat and MMD measured on days 1, 7, 14 and 20 of lactation. Gilts were weighed prior to being fed, and P2 backfat and MMD were measured over the last rib 65 mm down from the vertebrae by an experienced commercial operator using a 3.5 MHz linear probe (Ausonics Impact). Litter size was standardised to 9 piglets within 24 hours of farrowing, with piglets receiving only maternal milk as their feed source and weighed on days 1, 7, 13 and 20 of their mother's lactation. Maternal milk samples were collected on days 3, 13 and 20 of lactation and analysed for fat and protein content.

After weaning, sows were housed in groups of three or four. Boar exposure commenced on the fourth day after weaning, consisted of 15 minutes of full, physical boar contact and was conducted in a detection mating area (DMA). At their first oestrus after weaning, sows two artificial inseminations (AIs), 24 hours apart.

All AIs took place in the DMA, with fence-line contact with a boar during the procedure. Inseminations were performed as per standard industry practice using disposable spirette catheters, with each insemination consisting of an 80 ml dose of fresh, extended semen ($3 \times 10^9$ spermatozoa per inseminate; <4 days old). Semen used for this experiment was purchased from a commercial artificial insemination collection centre (SABOR Pty. Ltd, Clare, South Australia). Sows not detected in oestrus by 10 days after weaning were described as anoestrous.

Results

Sow Live Weight, P2 Backfat and MMD

Live weight, P2 backfat and MMD on day 1 of lactation were the same for the Control and Ractopamine treatments: 176.4±2.82 and 180.0±3.00 kg, 21.5±0.54 and 20.9±0.70 mm, and 55.5±0.86 and 56.8±0.77 mm, respectively. Live weight loss between days 1-7 and days 8 to 14 of lactation was similar for Control and Ractopamine sows; however, Ractopamine sows lost significantly less (P<0.05) live weight between days 15 and 20 of lactation (Table 3). Although the reduction in MMD in lactation was similar for the Control and Ractopamine treatments, Ractopamine sows lost significantly less (P<0.05) P2 backfat compared to Control sows (Table 3).

Reproductive Performance

Weaning-to-oestrus interval (WEI) was similar for Control and Ractopamine sows. However, there was a numerical, but not significant, reduction in the proportion of Control compared to Ractopamine sows exhibiting oestrus within 10 days of weaning (Table 3). A numerical, but not significant, increase (P=0.155) in the total number of piglets born at the second litter was observed for Ractopamine compared to Control sows (Table 3). However, there was a tendency (P=0.064) for the number of piglets born alive-at the second litter to be higher for Ractopamine compared to Control sows (Table 3).

Piglet Growth Characteristics

Individual piglet live weight gain between days 1 and 7 of lactation was unaffected by maternal dietary treatment (Table 4). However, average daily live weight gain (ADG) between days 7 and 14 of lactation tended (P<0.1) to be lower for piglets suckling Ractopamine sows compared to Control sows, while ADG between days 14 and 20 of lactation was significantly (P<0.01) lower for piglets suckling Ractopamine sows compared to piglets suckling Control sows (Table 4).

TABLE 3

Live weight, P2 backfat and MMD loss during lactation, weaning-to-oestrus interval (WEI), the proportion of sows exhibiting oestrous and second litter size for Control and Ractopamine sows

| | Control | Ractoparnine | Pooled SEM |
|---|---|---|---|
| Live weight loss in lactation (kg) | | | |
| Days 1-7   | 2.61  | 2.43    | 0.82 |
| Days 8-14  | 4.69  | 2.98    | 0.83 |
| Days 15-20 | 3.63a | 0.66[b] | 0.68 |

TABLE 3-continued

Live weight, P2 backfat and MMD loss during lactation, weaning-to-oestrus interval (WEI), the proportion of sows exhibiting oestrous and second litter size for Control and Ractopamine sows

|  | Control | Ractoparnine | Pooled SEM |
|---|---|---|---|
| P2 backfat loss in lactation (mm) | 3.85a | 2.44$^b$ | 0.46 |
| MMD loss in lactation (mm) | 2.7 | 2.1 | 0.74 |
| Weaning-to-oestrus (d) | 7.51 | 6.39 | 0.74 |
| Proportion sows exhibiting oestrus* | 0.75 | 0.95 | 0.08 |
| Proportion mated sows pregnant | 0.95 | 0.91 | 0.06 |
| 2$^{nd}$ litter size: | | | |
| Total born | 8.53 | 9.66 | 0.55 |
| Born alive | 8.11** | 9.48** | 0.51 |

$a^b$superscripts within row indicate significant difference; P < 0.05.
**P = 0.064
*Sow not exhibiting oestrus within 10 days of weaning were assigned a nominal weaning-oestrus of 15 days

TABLE 4

Average daily live weight gain (ADG) of piglets suckling Control and Ractopamine sows

| ADG (kg/d) | Control | Ractopamine | Pooled SEM |
|---|---|---|---|
| Days 1-7 | 0.2 | 0.2 | 0.004 |
| Days 8-14 | 0.25* | 0.24* | 0.005 |
| Days 15-20 | 0.30a | 0.26b | 0.008 |

$a^b$superscripts within row indicate significant difference; P < 0.05.
*P < 0.1

TABLE 5

Milk fat and protein on days 3, 13 and 20 of lactation for Control and Ractopamine sows

|  | Milk fat (g/l) | | | Milk protein (g/l) | | |
|---|---|---|---|---|---|---|
| Day of lactation | Cont. | Ract. | Pooled** | Cont. | Ract. | Pooled** |
| 3 | 69.2$^b$ | 80.4$^c$ | 74.8$^d$ | 45.2 | 45.7 | 45.5$^d$ |
| 13 | 65.7$^a$ | 64.7$^a$ | 65.2$^c$ | 41.6 | 39 | 40.3$^c$ |
| 20 | 66.1$^a$ | 65.8$^a$ | 65.9$^c$ | 41.5 | 39.9 | 40.7$^c$ |
| Pooled across day | 67.0* | 70.3* | | 42.8$^\dagger$ | 41.5$^g$ | |
| Pooled SEM | | | 2.18 | | | 0.72 |

$a^b$indicates significant interaction between day of lactation and dietary treatment; P < 0.05
$^{fg}$within row indicates significant difference between dietary treatments; P < 0.05.
*P = 0.064
$^{cd}$within column indicates significant differences between days of lactation; P < 0.05

Milk Composition

The protein content of milk was significantly lower for Ractopamine compared to Control sows (Table 5). Similarly the fat content of milk collected from Ractopamine sows tended (P=0.064) to be higher than in milk obtained from Control sows (Table 5). Day of lactation significantly affected milk protein and fat content (Table 5), with both fat and protein content significantly higher on day 3 of lactation compared to days 13 and 20.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and al combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A method of increasing or maintaining the reproductive performance of a sow or sow population comprising administering an effective amount of ractopamine from day 1 of lactation until weaning.

2. The method according to claim 1, wherein said reproductive performance is ovarian function.

3. The method according to claim 1, wherein said increase or maintenance of reproductive performance is a decrease in the weaning to oestrus interval of said sow.

4. The method according to claim 1, wherein said increase or maintenance of reproductive performance is an increase or maintenance of the number of sows in said sow population which return to oestrus at weaning.

5. The method according to claim 1, wherein said increase or maintenance of reproductive performance is an increase or maintenance of the number of progeny pigs weaned per sow in subsequent pregnancies.

6. The method according to claim 1 comprising:
 (i) administering an effective amount of ractopamine to a sow population during lactation such that the sow population exhibits a decreased weaning to oestrus interval compared to a sow population which has not been administered ractopamine; and
 (ii) inseminating sows in said sow population which exhibit oestrus.

7. The method according to claim 1 wherein the lactation diet is supplemented with between 5 and 20 ppm of ractopamine/unit of diet from day 1 of lactation until weaning.

8. The method according to claim 1 wherein the lactation diet is supplemented with 10 ppm of ractopamine/unit of diet from days 1 to 13 of lactation and 20 ppm of ractopamine/unit of diet from day 14 of lactation until weaning.

* * * * *